US010561899B2

(12) United States Patent
Florentine et al.

(10) Patent No.: US 10,561,899 B2
(45) Date of Patent: Feb. 18, 2020

(54) RESPONSIVE HIP STABILIZATION DEVICE

(71) Applicants: Tiffaney Florentine, Chicago, IL (US); Eugene Ernest Javier, Oak Lawn, IL (US)

(72) Inventors: Tiffaney Florentine, Chicago, IL (US); Eugene Ernest Javier, Oak Lawn, IL (US)

(*) Notice: Subject to any disclaimer, the term of this patent is extended or adjusted under 35 U.S.C. 154(b) by 0 days.

(21) Appl. No.: 16/041,782

(22) Filed: Jul. 21, 2018

(65) Prior Publication Data
US 2020/0023234 A1  Jan. 23, 2020

(51) Int. Cl.
| A63B 24/00 | (2006.01) |
| A63B 22/06 | (2006.01) |
| A63B 71/06 | (2006.01) |

(52) U.S. Cl.
CPC .......... *A63B 24/0003* (2013.01); *A63B 22/06* (2013.01); *A63B 24/0021* (2013.01); *A63B 71/0622* (2013.01); *A63B 2024/004* (2013.01)

(58) Field of Classification Search
None
See application file for complete search history.

(56) References Cited

U.S. PATENT DOCUMENTS

| 5,454,196 | A | * | 10/1995 | Gaines | E04F 11/002 14/69.5 |
| 5,900,592 | A | * | 5/1999 | Sohns | G01G 7/06 177/210 C |
| 2008/0280740 | A1 | * | 11/2008 | Knecht | A61B 3/113 482/146 |
| 2012/0264579 | A1 | * | 10/2012 | Klein | A63B 22/0015 482/146 |
| 2015/0302777 | A1 | * | 10/2015 | Campolo | A61H 1/0274 434/262 |
| 2016/0263424 | A1 | * | 9/2016 | LaCaze | A63B 23/0355 |
| 2019/0091510 | A1 | * | 3/2019 | Wallace | A63B 26/003 |
| 2019/0184227 | A1 | * | 6/2019 | Gouzenko | A63B 22/16 |
| 2019/0262209 | A1 | * | 8/2019 | Grbic | A61H 1/005 |

* cited by examiner

*Primary Examiner* — Stephen R Crow
(74) *Attorney, Agent, or Firm* — Andrew Morabito

(57) ABSTRACT

The present invention is a responsive exercise device comprising a base having a first end and a second end, wherein the base has a plurality of compartments, a plurality of measurement sensors, a plurality of support panels secured to the base over the first set of the plurality of compartments, a plurality of positioning rails secured to the plurality of support panels, wherein the positioning rails have a plurality of openings sized to fit a bearing, a plurality of bearings positioned within the openings of the plurality of rails and between the support panels, wherein the plurality of bearings are retained in the openings and freely rotate; a first spring assembly positioned distal to the first end of the base, a second spring assembly positioned distal to the second of the base comprising, a plurality of plates positioned over the plurality of bearing assemblies and mechanically.

20 Claims, 8 Drawing Sheets

RESPONSIVE HIP STABILIZATION DEVICE

BACKGROUND

The present invention relates generally to the field of a stabilization devices. More specifically, the invention relates to a device that enables individuals with sub-optimal posterior muscular recruitment to stabilize the femur within the pelvic cavity to force optimal posterior muscular recruitment, and a neutral spine, alleviating both anterior and posterior pelvic tilt while standing, sitting or when engaging in functional exercise.

Physical inactivity, and specifically sitting, results in poor neural output to the posterior chain, shortened hip flexors and gluteal atrophy, leading to a sub-optimal hip stability, anterior pelvic tilt (APT) and posterior pelvic tilt (PPT), ultimately, causing muscular reciprocal inhibition, poor movement patterns and often physical pain.

The gluteals, hamstrings, external obliques, rectus abdominus muscles become lengthened, weakened and underactive, and the psoas, rectus femoris, tensor fascia latae, erector spinae become shortened and overactive.

The muscular inhibition from APT and PPT leads to sub-optimal muscle recruitment and poor movement patterns when performing daily functional activities (squatting, standing, pressing, etc.) And when performing the same functional movements during exercise. This poor form leads to back and knee discomfort and pain, and often many other downstream physical ailments that currently plague the U.S. Population. It's estimated that 80% of the U.S Population experiences back pain in their lives and will continue to worsen due to sitting.

Optimizing proper muscle recruitment while performing daily functional activities and/or exercise through verbal cueing is extremely difficult due to muscular inhibition and motor pattern deficiencies driven by neural reliance on the psoas, rectus femoris, tensor fascia latae, erector spinae become shortened and overactive during movement.

Optimizing proper muscle recruitment while performing daily functional activities and/or exercise through verbal cueing is extremely difficult due to muscular inhibition and motor pattern deficiencies. Due to extended sitting the body develops a neural reliance on the psoas, rectus femoris, tensor fascia latae and erector spinae, which become shortened and overactive during movement, causing sub-optimal recruitment of the posterior chain, leading to poor movement patterns, pain and injury of the knees and lower back due to excessive loading.

Since neural output to the posterior chain is deficient as a result of sitting, mechanical stability is leveraged by stabilizing the femur within the pelvic cavity, thus forcing the recruitment of the gluteal, hamstring, external obliques, rectus abdominus muscles.

SUMMARY

In a first embodiment, the present invention is a responsive exercise device comprising; a base having a first end and a second end, wherein the base has a plurality of compartments, a plurality of measurement sensors positioned within a first set of the plurality of compartments, a plurality of support panels secured to the base over the first set of the plurality of compartments, a plurality of positioning rails secured to the plurality of support panels, wherein the positioning rails have a plurality of openings sized to fit a bearing, a plurality of bearings positioned within the openings of the plurality of rails and between the support panels, wherein the plurality of bearings are retained in the openings and freely rotate, a first spring assembly positioned distal to the first end of the base, comprising, a first plurality of springs are in a state of tension having a first end a second end, a spring plate connected to the first end of the first plurality of springs, a spring plate connected to the second end of the first plurality of springs, a second spring assembly positioned distal to the second of the base comprising; a second plurality of springs are in a state of compression having a first end a second end, a spring plate connected to the first end of the second plurality of springs, a spring plate connected to the second end of the second plurality of springs, and a plurality of plates positioned over the plurality of bearing assemblies and mechanically connected to the sensors, the first spring assembly, and the second spring assembly.

The present invention further comprising; a first light source attached to the first end of the base, and a second light source attached to the first end of the base.

In a second embodiment of the present invention, a responsive exercise device comprising; a base having a first edge and a plurality of compartments, a plurality of sensors positioned, wherein one of the plurality of sensors are placed within each compartment of a first set of the plurality of compartments, a plurality of support panels having a first surface, wherein the plurality of support panels are secured directly atop the first set of the plurality of compartments of the base, a plurality of positioning rails having a plurality of openings along a central axis secured to the first surface of the plurality of support panels, a plurality of bearings positioned within the openings of the plurality of rails and between the first surface of the support panels, thus the plurality of bearings are retained in the openings and are able to freely rotate in position, a first spring assembly positioned distal to the first end of the base, comprising; a first plurality of springs are in a state of tension having a first end a second end, a spring plate connected to the first end of the first plurality of springs, a spring plate connected to the second end of the first plurality of springs, a second spring assembly positioned distal to the second of the base comprising, a second plurality of springs are in a state of compression having a first end a second end, a spring plate connected to the first end of the second plurality of springs. a spring plate connected to the second end of the second plurality of springs, and a plurality of plates disposed directly over each of the support panels and each of the plurality of plates is mechanically connected to one of the sensors, and a first set of the plates connected to the first spring assembly, and a second set of the plates connected to the second spring assembly.

In yet a third embodiment, the present invention a responsive exercise device comprising; a base having a first quadrant, a second quadrant, a third quadrant, a fourth quadrant, a first edge, a second edge, a plurality of sensors, wherein one of the plurality of sensors are placed within each of the quadrants, a plurality of support panels having a first surface, wherein one of the plurality of support panels are secured in each quadrant and are substantially aligned, a plurality of positioning rails having a plurality of openings along a central axis secured to the first surface of the plurality of support panels arranged in parallel, a plurality of bearings positioned within the openings of the plurality of rails and the bearings are able to freely rotate in position, a first spring assembly positioned between the first quadrant and the second quadrant distal to the first end of the base, comprising, a first plurality of springs are in a state of tension having a first end a second end, a spring plate connected to the first end of the first plurality of springs, a spring plate connected to the second end of the first plurality of springs, a second spring assembly positioned between the third quadrant and the fourth quadrant and distal to the second of the base comprising, a second plurality of springs are in a state of compression having a first end a second end, a spring plate connected to the first end of the second plurality of springs, a spring plate connected to the second end of the second plurality of springs, and a plurality of plates, wherein one of the plurality of plates is disposed directly over each of the support panels and mechanically connected to the sensor positioned within that quadrant, and the plates positioned over the first quadrant and the second quadrant are mechanically connected to the first spring assembly and the plates positioned over the third quadrant and the fourth quadrant are mechanically connected to the second spring assembly.

DETAILED DESCRIPTION

A preferred embodiment of the present invention is now described with reference to the figures, where like reference numbers indicate identical or functionally-similar elements. While specific configurations and arrangements are discussed, it should be understood that this is done for illustrative purposes only. A person skilled in the relevant art will recognize that other configurations and arrangements can be used without departing from the spirit and scope of the invention.

As will be appreciated by one skilled in the art, aspects of the present invention may be embodied as device. Accordingly, aspects of the present invention are designed to create a responsive exercise device to assist with stabilization and improve the persons posture during certain exercises. The exercise device aid individuals with creating, understanding and indicating self-generated mechanical stability of the hip joint through external rotation of the femur within the pelvic capsule.

The present invention seeks to solve these problems by providing a responsive device configured to alert the user when they are actively generating mechanical stability of the femur within the pelvic cavity through external rotation while and successfully distributing weight in the heels. The exercise device also assists in alleviates APT and PPT while standing and when performing functional movements (squats, deadlifts, presses, etc.) and other types of exercise or movement with both feet grounded.

The present invention will now be described in detail with reference to the figures.

Figure 1:
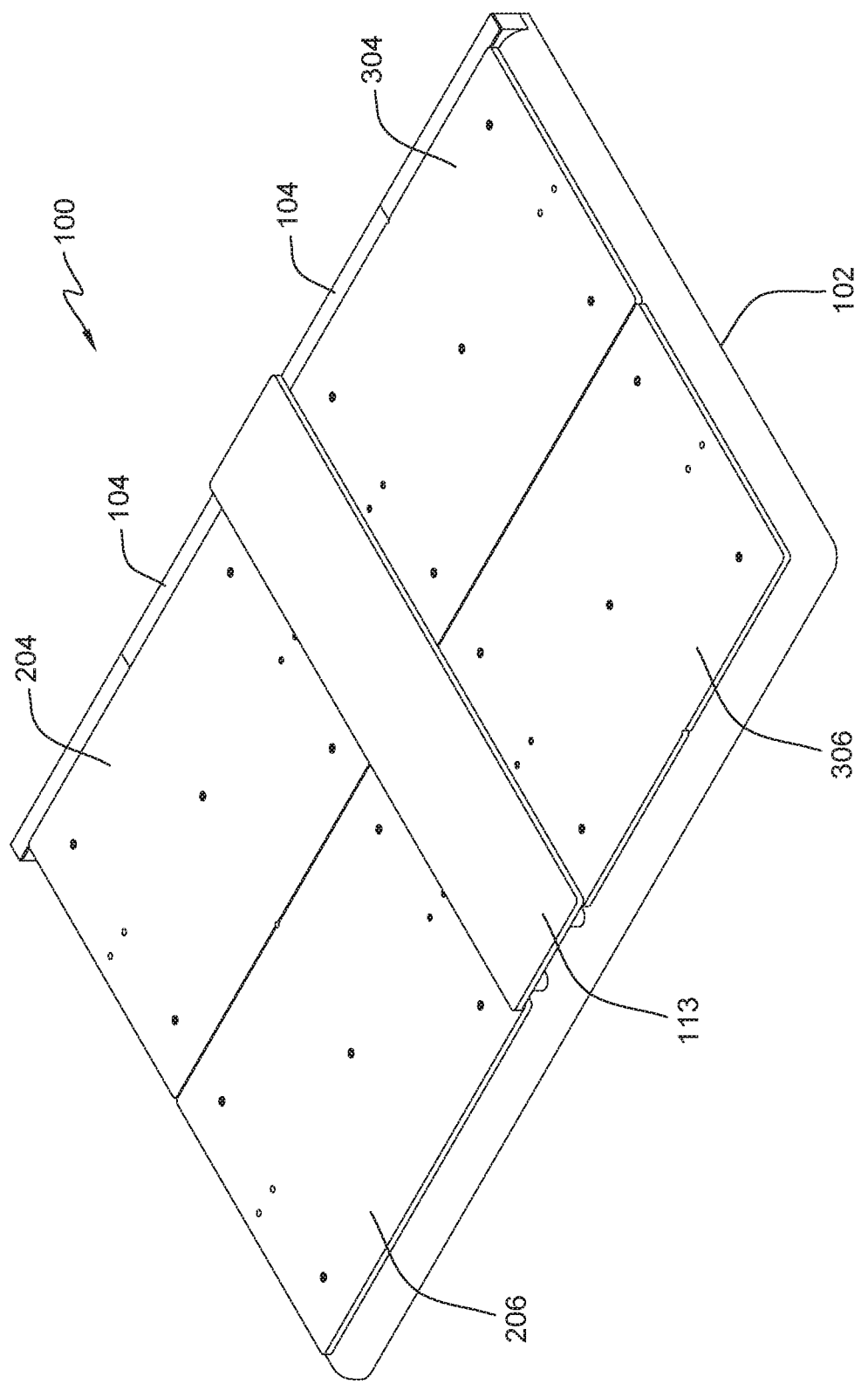
FIG. 1 depicts a perspective view of a responsive exercise device, in accordance with one embodiment of the present invention.

FIG. 1 depicts a perspective view of a responsive exercise device 100, in accordance with one embodiment of the present invention. Shown in the depicted figure is the responsive exercise device 100, a base 102, a front left plate 204, a rear left plate 206, a front right plate 304, a rear right plate 306, light sources 104, and cover 113.

The front left plate 204, rear left plate 206, front right plate 304, rear right plate 306 (hereinafter referred to as plates) provide the structure and surfaces in which the user positions themselves on when using the device 100. The plates are electronically connected to sensors 500 so that when the user performs an action that is registered by the sensor, the sensor sends a signal to the processor 110 to turn off, turn on, or adjust one or more of the light sources 104 and/or 106. The plates may be molded of a high-strength-plastic material. Alternatively, plates can be formed from a fiberglass, metal, wood, or other rigid materials. In some embodiments, the plates (204, 206, 304, and 306) have a coating to increase the user's contact with the plates. In the depicted embodiment, the plates (204, 206, 304, and 306) are identical to provide for interchangeability among all plates. In some embodiment, the plates are molded of a high-strength-plastic material. Alternatively, the plates can be formed from a fiberglass, metal, wood, or other rigid materials.

The cover 113 provides protection for the electronic components and to allow easy access to these electronic components for maintenance. The cover 113 is detachably secured to the device 100 to allow for quick attachment and detachment. In some embodiment, cover 113 is molded of a high-strength-plastic material. Alternatively, cover 113 can be formed from a fiberglass, metal, wood, or other rigid materials.

The light source 104 provides a visual identifier for the user when the plates (e.g. 204, 206, 304, and 306) are being displaced from their initial position. The visual identifier is projected upwards towards the user. In the depicted embodiment, the light source 104 is positioned along a front edge (e.g. edge in front of the user whom is properly positioned on the device 100). The light source 104 is in electrical communication with a processor 110, so that when sensors 500 are activated, the sensors communicate with processor 110. The light source 104, may be activated when the plates (204, 206, 302, 306) reach a predetermined displacement from their initial position. For example, the light source 104 may be activated when the user is not in the proper position. In another embodiment, the light source 104 is activated when the user is in the proper position. In the depicted embodiment, the light source 104 is comprised of two (2) light bars positioned on the front edge of the device 100. In one embodiment, one of the light sources 104 is associated with the sensors 500 communicating with the front left plate 204, a rear left plate 206, and the second light source 104 communicates with the sensors 500 that are in communication with the front right plate 304, a rear right plate 306. In additional embodiments, additional lights sources 104 may be incorporated into the device 100 and each sensor 500 communicates with one light source 104. Thus, the responsive exercise device 100 provides visual notification to the user if their stance is proper (e.g. the user is spreading their feel and pulling their heels). The light source 104 may optionally be any sort of a lamp (incandescent, neon, etc.) or solid-state light emitting device/chip, like a LED (Light Emitting Diode), LASER chip, an electroluminescent device or others. LED is preferable in view of its low cost, low power, durability, size and range of available emission colors. In some embodiments, the color of the light source 104 is associated with how much displacement is occurring with the plates.

Figure 2:
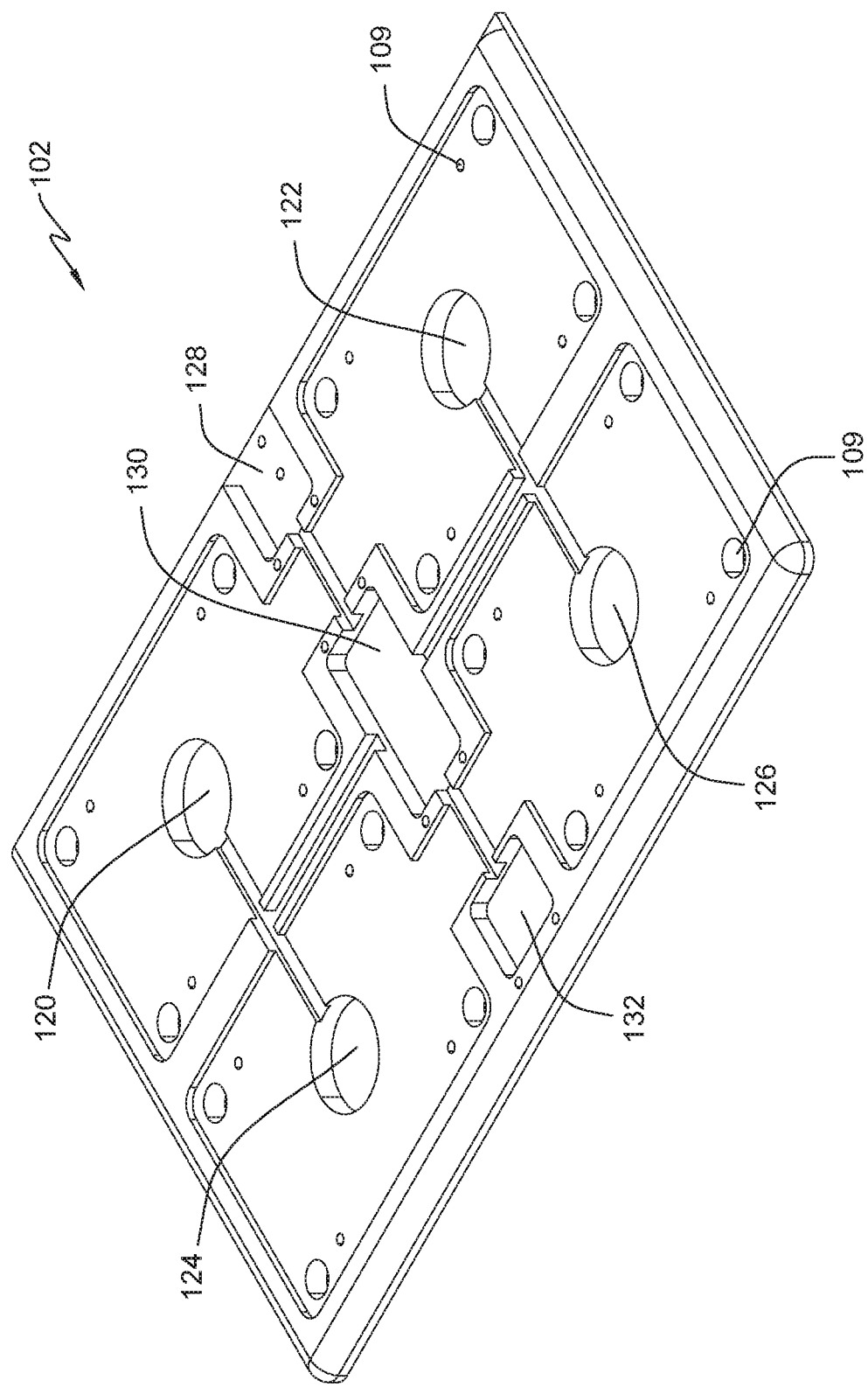
FIG. 2 depicts a perspective view of a base plate of the responsive exercise device, in accordance with one embodiment of the present invention.

FIG. 2 depicts a perspective view of a base 102 of the responsive exercise device 100, in accordance with one embodiment of the present invention.

The base 102 serves as the structure support for the responsive exercise board 100, to secure the components, and to house the various electronic elements. Openings 120, 122, 124, 126 are sized to receive sensors 500. In the depicted embodiment, the openings 120, 122, 124, and 126 extend completely through the base 102. In additional embodiments, openings 120, 122, 124, and/or 126, may not extend through the base 102, but provide access to the sensors 500. Cavity 128 is sized to fit a second light source 106. Cavity 130 is designed to fit the power source 108. Cavity 132 is sized to fit the processor 110.

In the depicted embodiment, a plurality of channels connects the cavities to provide clear passage for cables and wiring to connect the various electronic components. This includes the sensors 500, the light sources 104 and 106, the power source 108, and the processor 110. In the depicted embodiment, the base 102 also has openings to for receiving various fasteners to secure different components to the base 102. It would be apparent to one skilled in the relevant art that alternative means other than fasteners may be used, for example rivets, or more permanent welds. In various embodiments, these openings may be in a variety of locations, of various sizes, and may be threaded depending on the fastener which is to be inserted in or through the opening 109.

In the depicted embodiment, the base 102 is divided into four quadrants (front left, front right, rear left, rear right) and these quadrants are substantially identical. The four identical quadrants allow for interchangeability of all the components between the four quadrants. In additional embodiments, the quadrants may have different designs, layouts, and to receive different components.

In some embodiment, base 102 is molded of a high-strength-plastic material. Alternatively, base 102 can be formed from a fiberglass, metal, wood, or other rigid materials. The base 102 can be formed to include support members on a bottom surface of base 102. In these embodiments, the base supports are downwardly projecting extensions on the bottom surface of base 102. It would be apparent to one skilled in the relevant art that other support structures could also be used to provide added stability and rigidity to base 102.

Figure 3:
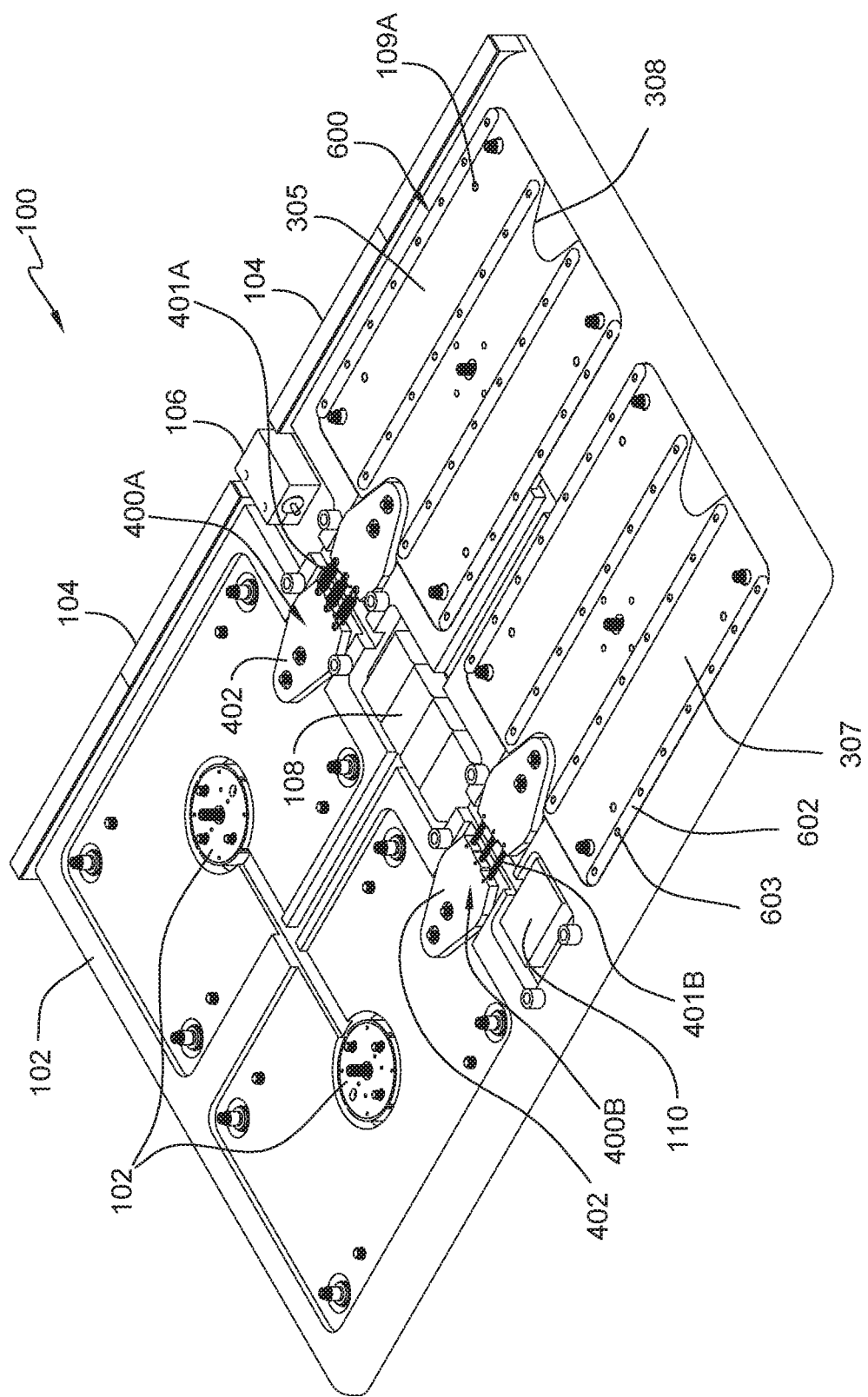
FIG. 3 depicts a perspective view of a partial assembly of the responsive exercise device, in accordance with one embodiment of the present invention.

FIG. 3 depicts a perspective view of a partial assembly of the responsive exercise device 100, in accordance with one embodiment of the present invention. In the depicted embodiment the front left plate 204, rear left plate 206, front right plate 304, rear right plate 306 are removed exposing various internal components. Visible is bearing assemblies 600, a lower rear right panel 307, and a lower front right panel 305. A rear left plate and a front left plate have been removed but are substantially identical to the panels 305 and 307 in design and features.

The light source 106 provides a visual identifier for the user when plates (204, 206, 304, and 306) are in their respective proper position. In the depicted embodiment, the light source 106 is positioned along a front edge (e.g. edge in front of the user whom is properly positioned on the device 100) and projects a visual indicator onto the floor or ground in front of the responsive exercise device 100. The light source 106 is in electrical communication with the processor 110, so that when the sensor(s) 500 communicate with the processor 110 and the plates (204, 206, 304, and 306) are in the proper position (e.g. when the user has the proper positioning of both of their feet), the light source 106 is activated and displays a visual indicator to the user on the ground in front of them. The use of the light source 106 assists the user in not having to look directly at their feet to confirm the proper positioning of their feet if the exercise they are performed would make it difficult to look directly down. The light source 106 may optionally be any sort of a lamp (incandescent, neon, etc.) or solid-state light emitting device/chip, like a LED (Light Emitting Diode), LASER chip, an electroluminescent device or others. LED is preferable in view of its low cost, low power, durability, size and range of available emission colors. In some embodiments, the color of the light source 106 is associated with how much displacement is occurring with the plates.

In some embodiment, the light source 106 projects a visual identifier to the user on the ground in front of the user. The position and intensity of the visual identifier may vary. In some embodiments, the visual identifier is active only when the user is in the correct position. In some embodiments, the visual identifier is adjusted based on the degree of error in the user's posture. For example, the farther from the "ideal" position the user is in, the brighter the visual identifier is to provide a greater visual que to the user to correct their stance.

The lower panels 305 and 307 (and a lower rear left panel 207, and a lower front left panel 205 not shown) provide structural support for a cover for the channels, the various compartments of the base 102, and provide a platform for the bearing assemblies 600 to be mounted to. The lower panels have a cutout 308 which is positioned along a central axis of the lower panels on opposing sides. The cutout 308 provides adequate space for the spring assembly 400 to fit within, so that when the plates (204, 206, 304, and 306) are positioned over the respective lower panels, that the spring assemblies 400 can be fastened to plates (204, 206, 304, and 306). The cutout 308 also provides additional space for the plates to displace a predetermined distance from their original position. The cutout 308 is on opposing sides of the lower panels to allow for the lower panels to be reversible and interchangeable among the four quadrants. The lower panels have a plurality of openings 109A to allow for insertion of fasteners.

In some embodiment, the lower panels are molded of a high-strength-plastic material. Alternatively, lower panels can be formed from a fiberglass, metal, wood, or other rigid materials.

In one embodiment, the spring assembly 400A provides tension to the connected plates (204 and 304). This assists the user in keeping their toes from spreading apart. The spring assembly 400B provides a compression force to the connected plates (206 and 306). This assists the user by keeping their heels together. In the depicted embodiment, the spring assemblies 400A and 400B are comprised of a plurality of springs 401A and 401B respectively, which are connected to a spring plate 402. The springs 401A are tension springs or extension springs. Springs 401B are compression springs. In additional embodiments, the springs 401A may exert a compression force and springs 401B maybe in a state of tension. In the depicted embodiment, the spring plates 402 are secured to the plates (204, 206, 304, and 206) by fasteners. The springs 401A and 401B connected the two plates 402 together to complete the spring assemblies 400A and 400B. The springs 401 are removed, so that different springs with varying spring constant values based on the desired resistance for the user or trainer. In some embodiment, spring plates 402 are molded of a high-strength-plastic material. Alternatively, spring plates 402 can be formed from a fiberglass, metal, wood, or other rigid materials.

Sensors 500 are shown inserted into the openings (124 and 120) of the base 102. The sensor 500 extends through the lower panels and is mechanically connected to the respective plate. This allows the sensor 500 to be protected while the device 100 is in use.

Bearing assemblies 600 are comprised of a rail 602 with a plurality of openings and a plurality of bearings 603 fitted into the openings. The rails 602 are secured to the lower panels and the bearings 603 are able to move freely within the openings. The stationary yet freely rotating bearings 603 permit the respective plate (204, 206, 304, or 306) to move independently. The bearing assemblies 600 are secured to the lower panels. In the depicted embodiment, a set of four bearing assemblies 600 are attached to each lower panel and are substantially parallel with the front and rear edges of the base 102. In additional embodiments, various layouts and number of bearing assemblies 600 may be attached to each lower panel.

Figure 4:
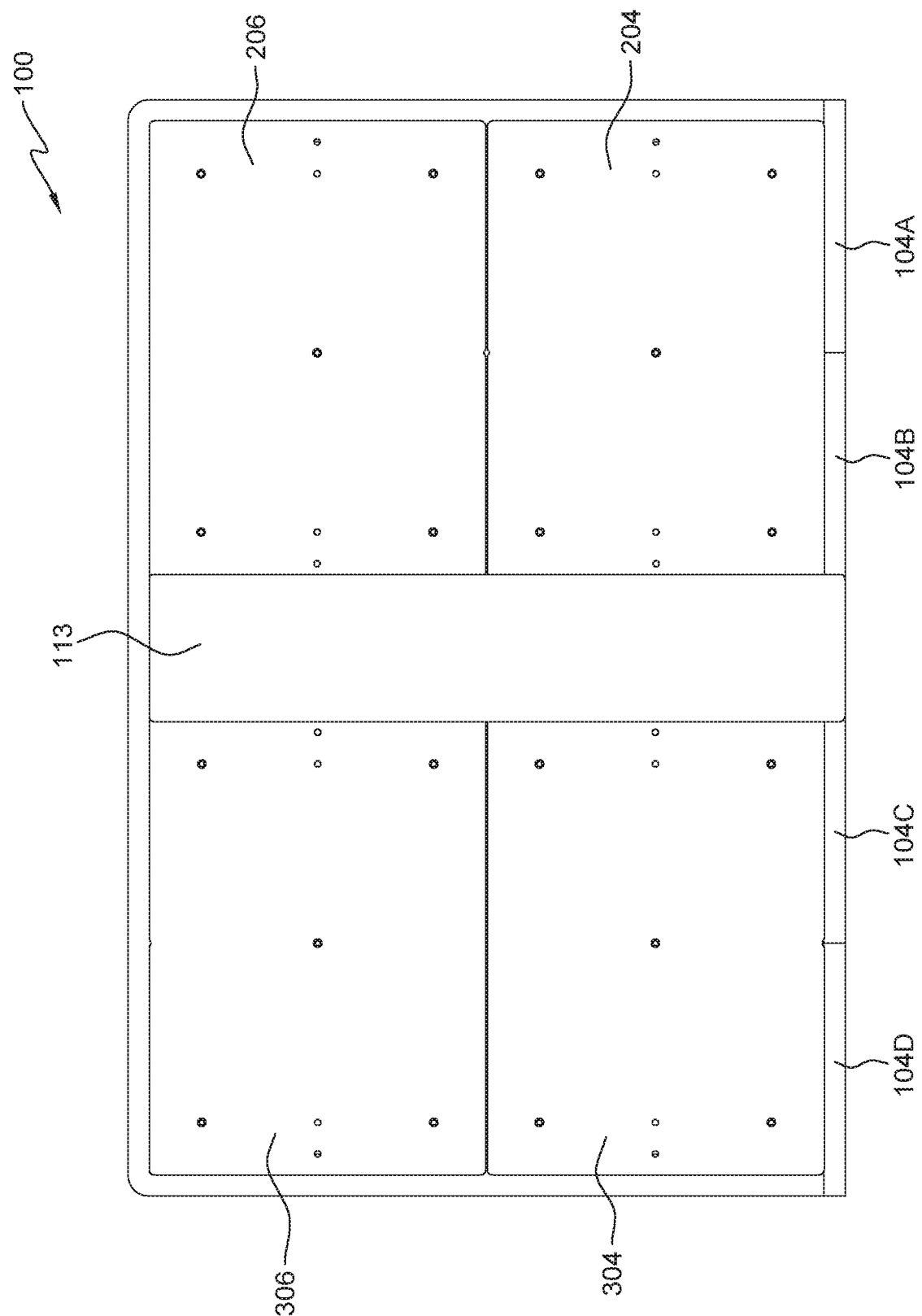
FIG. 4 depicts a top view of the responsive exercise device, in accordance with one embodiment of the present invention.
Figure 5:
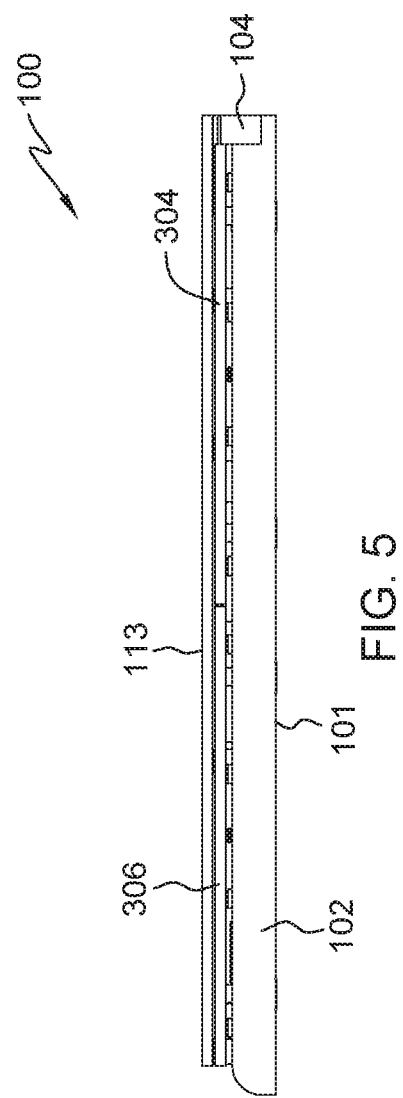
FIG. 5 depicts a side view of the responsive exercise device, in accordance with one embodiment of the present invention.

FIGS. 4 and 5 depicts a top view and side view respectively of the responsive exercise device 100, in accordance with one embodiment of the present invention. Depicted are the plates (204, 206, 304, and 306), wherein cover 113 overlaps a portion of the plates to cover the internal electrical components. In the depicted embodiment, the light source 104 is separated into four different sections 104A, 104B, 104C, and 104D. Each of the light source sections are connected to one of the plates 204, 206, 304, or 306. This allows the user to have a visual indicator if it is there right heel, right toes, left heel, or left toes which are not in the proper position. In the depicted embodiments, the base 102 bottom surface 101 is shown.

Figure 6:
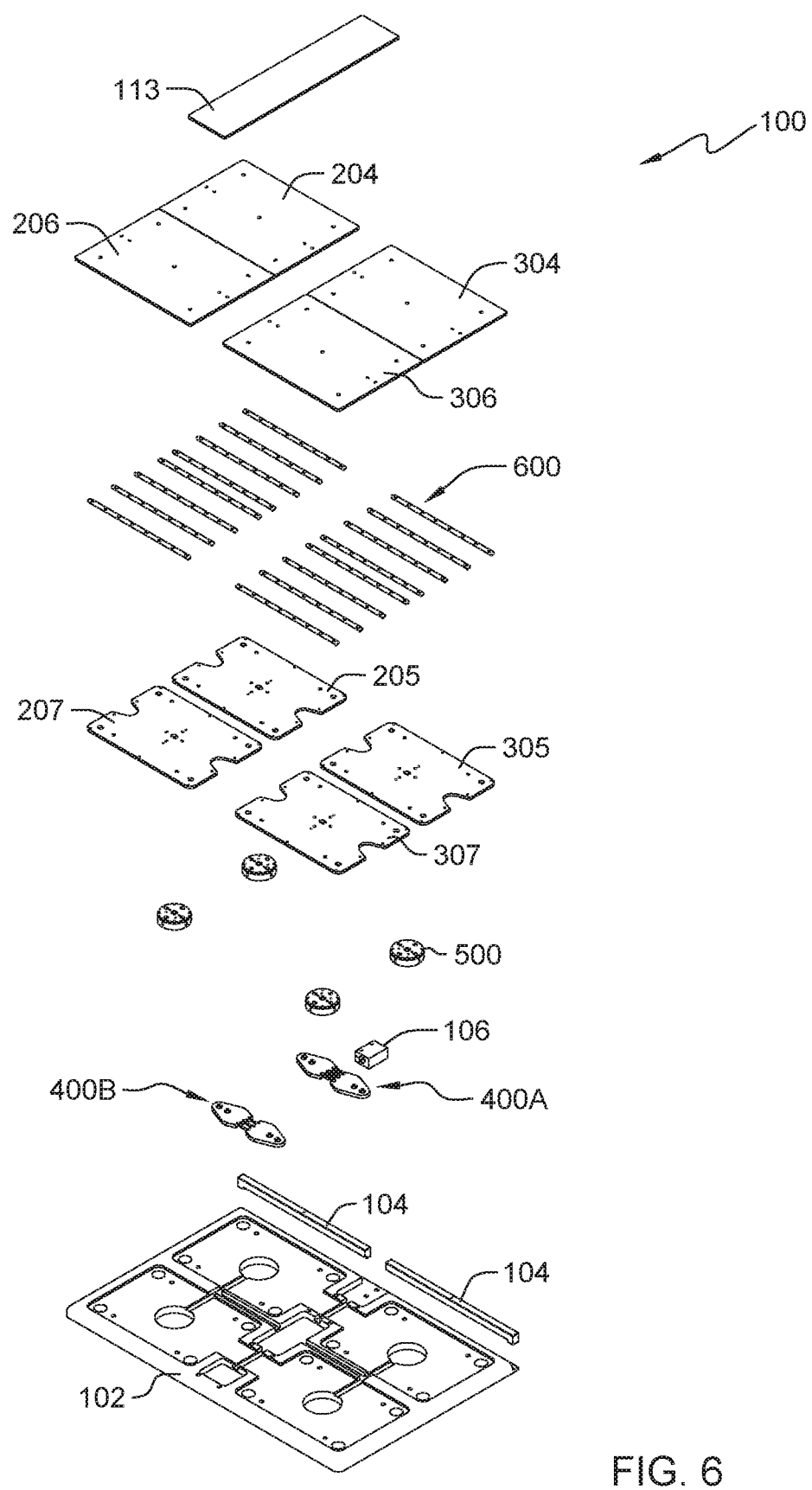
FIG. 6 depicts an exploded view of the responsive exercise device, in accordance with one embodiment of the present invention.
Figure 7:
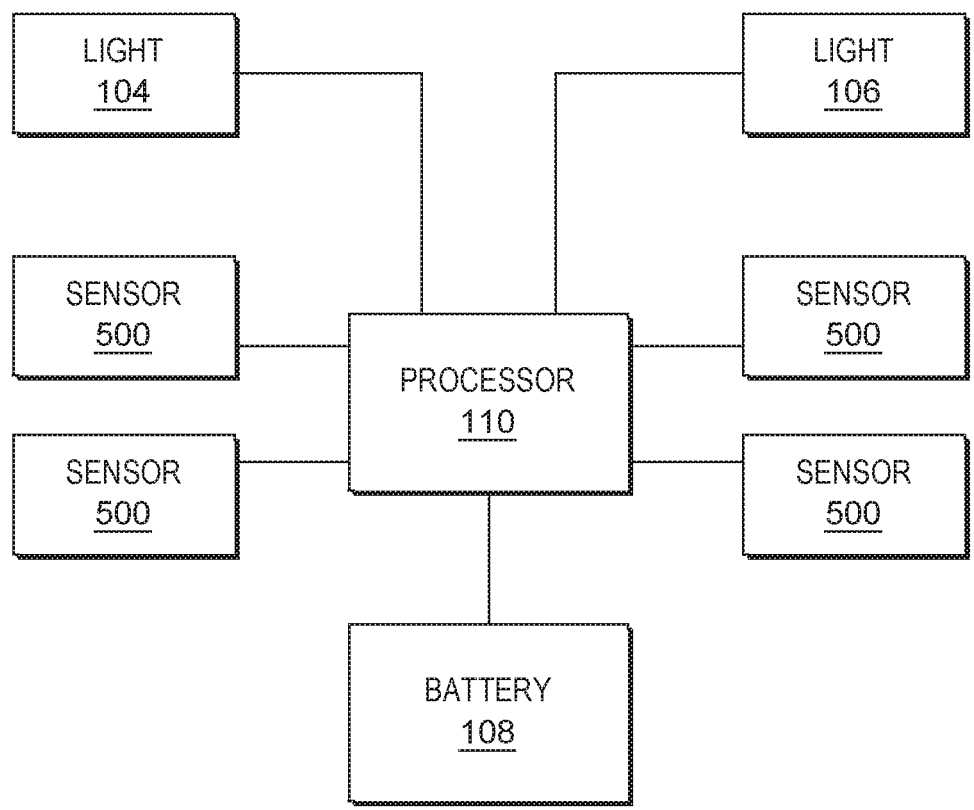
FIG. 7 depicts a schematic drawing of the electrical components of the responsive exercise device, in accordance with one embodiment of the present invention.

FIG. 6 depicts an exploded view of the responsive exercise device 100, in accordance with one embodiment of the present invention. In the depicted embodiment, the device 100 is shown in four identical sections. For example, plate 204 has four bearing assemblies 600 positioned between plate 204 and lower panel 205, a sensor 500 secured below the lower panel 205. This structure is carried through with plates 206, 304, and 306.

With this structure, the plates are able to move freely. In one embodiment the plates are able to move parallel to the springs 401A and 401B. In additional embodiments, the plates are able to move in more than one direction (e.g. perpendicular to the springs 401A and 401B). In some embodiments, the plates are able to move up and down relative to the base 102 bottom surface 101. Each plate is able to move independently of the other plates. This allows for the user to have more control over their position while using the device 100. The springs 401A and 401B provide a resistance force against a person's natural tendency to move their feet or position their bodies in a less than desired position.

Figure 8:
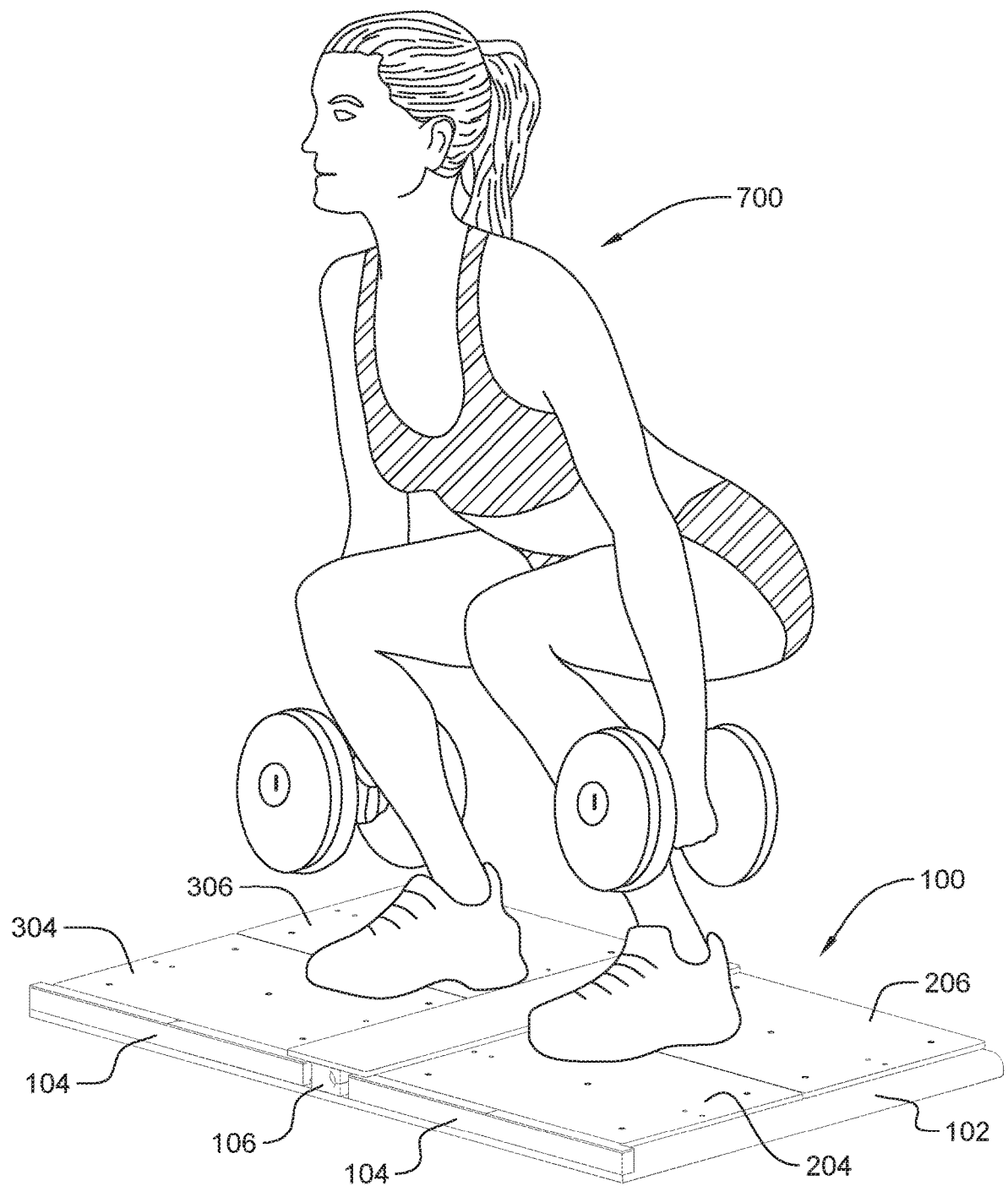
FIG. 8 depicts an image of a user on the responsive exercise device, in accordance with one embodiment of the present invention.

FIG. 8 depicts a schematic drawing of the electrical components of the responsive exercise device 100, in accordance with one embodiment of the present invention. In the depicted embodiment, the responsive exercise device 100 has two (2) light sources 104, one (1) light source 106, four (4) sensors 500, a processor 110, and a battery 108. In additional embodiments, various other electronic components may be incorporated into the electrical system known to one skilled in the art.

The sensors 500 converts the mechanical response of the movement or displacement of the plates (204, 206, 304, and 306) to an electrical connection with the processor 110. In the depicted embodiment, the sensors 500 act independently of one another. Each of the sensors is connected to one of the plates. Once one of the plates has reached a predetermined displacement or movement from its initial position, an electrical signal is sent to the processor 110, this signal is then used to determine if the light sources 104 and 106 are active or inactive. In the depicted embodiment, the sensors 500 are positioned within an opening in the base 102 and secured to the respective plate through an opening in the respective panel.

The power source 108 provides the necessary energy to power the processor 110, sensors 500, and light sources 104 and 106. The power source 108 may be made from various types of batteries may be used, such as alkaline, lithium, zinc-carbon, and the like. The power source 108 may also be rechargeable and have the necessary ports to connect to a power source. The power source 108 may be various batteries known to those skilled in the art.

The processor 110 receives the information from the sensors 500 and controls the activation of the light sources 104 and 106. The processor 110 determines which light source to activate and the intensity of the light source based on the received data from the sensors 500. The present invention includes a system, a method, and/or a computer. The computer may include a computer readable storage medium (or media) having computer readable program instructions thereon for causing a processor to carry out aspects of the present invention.

In additional embodiments, a speaker may be included in the electrical system to give an audible notification that the user is not in the proper position. In yet another embodiment, a vibration motor to provide a haptic feedback to the user if they are not in the proper position, or when they achieve the proper position.

FIG. 8 depicts an image of a user on the responsive exercise device, in accordance with one embodiment of the present invention. For exemplary purposes, the method of operation of the device 100 in one embodiment is described. Additional methods of operation and variations to the described example may also be employed.

The user stands with their right forefoot on plate 304, their right heel on plate 306, their left forefoot on plate 204, their left heel on plate 206. When the user begins to adjust or move their feet (either forefoot or heel) the sensor 500 attached to the respective plate is able to track the user's movement through the plate displacement due to the plate being placed over the bearing assemblies 600. As the plate shifts from its initial position, the sensors 500 provide the signal to the processor 110, which activates the light source(s) 104 and/or 106. While the user is moving the plates, the spring assembly 400 are applying a resistance to the movement. In some embodiments, the spring assemblies 400 are assisting the user in moving their feet from the initial position. In some embodiments, if the user moves their feet or part of their foot beyond a threshold position the sensors 500 sends a signal to deactivate the light source(s) 104 and/or 106.

In one example, when the user has proper positioning of their feet the first light source 106 activates a green light and the second light source 108 displays an image on the ground in front of the user for an additional reference to indicate their proper position. In some embodiments, if the user does not have proper positioning of their feet, foot, or part of their foot the light source(s) 106 and/or 108 display a different color (e.g. red) to warn the user of their improper form.

The user can use the device during a physical activity, while standing, or while sitting.

a. Physical Activity/"Working Out":

The device can be utilized for all physical activity where both feet come into contact with the ground simultaneously, and when bearing weighted objects.

The user performs the following steps:
1. Standing position; feet positioned straight forward, heel, ball of foot and first toe (hallux) and second toe (long toe) in contact with the ground, knees fully extended, hips fully extended, shoulders stacked over hips, head and neck in neutral position stacked over hips.
2. Gluteus muscles active/squeezed.
3. First toe (hallux) and second toe (long toe) create force by pulling the ground apart actively driving into the ground while pulling outward to generate external rotational force, creating external rotational force and stability of the femur in the hip cavity.
4. Heels stay grounded and generate force by pulling inward, in the opposite direction of the external force created by the ball of the foot.
5. User has the option to move to hip and knee flexion by moving the hips backwards, guiding knees over knee track-line indicators visually depicted on device, while maintaining external rotational force as outlined in item 3, and while maintaining the distance between the bottom of the rib cage and navel to create a stable hip position to ensure posterior musculature recruitment and proper movement, alleviating possibility of strain and pain on the lower back and knee joints, and alleviating the likelihood of PPT and APT.

a. Standing:

The device can be utilized for all standing, static activities.

The user performs the following steps:
1. Standing position; feet positioned straight forward, heel, ball of foot and first toe (hallux) and second toe (long toe) in contact with the ground, knees fully extended, hips fully extended, shoulders stacked over hips, head and neck in neutral position stacked over hips.
2. Gluteus muscles active/squeezed.
3. First toe (hallux) and second toe (long toe) create force by pulling the ground apart/actively driving into the ground while pulling outward to generate external rotational force, creating external rotational force and stability of the femur in the hip cavity.
4. Heels stay grounded and generate force by pulling inward, in the opposite direction of the external force created by the ball of the foot.

b. Sitting:

The device can be utilized for all sitting, static activities where both feet are in contact with the ground.

The user performs the following steps:
1. sitting position; heel, ball of foot and big toe in contact with the ground.
2. hips in flexion position with shoulders stacked over hips, while maintaining the natural distance (identified when standing) from the bottom of the rib cage, to maintain a neutral spine.
3. knees in flexion position with knee stacked directly over the heels with the knee joint pointing towards the 3rd and 4th toe.
4. Ball of foot and big toe create force by pulling the ground apart/actively driving into the ground while pulling outward to generate external rotational force to activate glutes.
5. Heels stay grounded and generate force by pulling inward, in the opposite direction of the external force created by the ball of the foot.

While this invention has been described in conjunction with the specific embodiments outlined above, it is evident that many alternatives, modifications and variations will be apparent to those skilled in the art. Accordingly, the preferred embodiments of the invention, as set forth above, are intended to be illustrative, not limiting. Various changes may be made without departing from the spirit and scope of this invention.

The invention claimed is:

1. A responsive exercise device comprising:
a base having a first end and a second end, wherein the base has a plurality of compartments;
a plurality of measurement sensors positioned within a first set of the plurality of compartments;
a plurality of support panels secured to the base over the first set of the plurality of compartments;
a plurality of positioning rails secured to the plurality of support panels, wherein the positioning rails have a plurality of openings sized to fit a bearing;
a plurality of bearings positioned within the openings of the plurality of rails and between the support panels, wherein the plurality of bearings are retained in the openings and freely rotate;
a first spring assembly positioned distal to the first end of the base, comprising:
a first plurality of springs are in a state of tension having a first end a second end,
a spring plate connected to the first end of the first plurality of springs,
a spring plate connected to the second end of the first plurality of springs,
a second spring assembly positioned distal to the second of the base comprising:
a second plurality of springs are in a state of compression having a first end a second end,
a spring plate connected to the first end of the second plurality of springs,
a spring plate connected to the second end of the second plurality of springs; and
a plurality of plates positioned over the plurality of bearing assemblies and mechanically connected to the sensors, the first spring assembly, and the second spring assembly.

2. The responsive exercise device of claim 1, further comprising a first light source attached to the first end of the base.

3. The responsive exercise device of claim 2, wherein when at least one of the plurality of plates displaces from its original position a predetermined distance or rotate a predetermined degree from the original position, the first light source is activated.

4. The responsive exercise device of claim 3, further comprising a second light source attached to the first end of the base.

5. The responsive exercise device of claim 4, wherein when at least one of the plurality of plates move a predetermined distance or rotate a predetermined degree, the second light source is activated.

6. The responsive exercise device of claim 5, further comprising an electrical system to connect the sensors with the first and second light source, wherein the electrical system is positioned within a second set of the plurality of compartments.

7. The responsive exercise device of claim 6, further comprising a cover secured to the plurality of plates over the second set of compartments of the plurality of compartments.

8. The responsive exercise device of claim 1, wherein the base has a plurality of channels connecting the second set of compartments.

9. The responsive exercise device of claim 1, wherein the support plates have a cutout on a first and second side, wherein the cutout is sized to receive the spring plate.

10. The responsive exercise device of claim 3, wherein when the second light source is activated, the visual indicator is projected in upwards from the top surface of the plates.

11. The responsive exercise device of claim 5, wherein when the second light source is activated, the visual indicator is projected in front of the first edge of the base.

12. A responsive exercise device comprising:
a base having a first edge and a plurality of compartments;
a plurality of sensors positioned, wherein one of the plurality of sensors are placed within each compartment of a first set of the plurality of compartments;
a plurality of support panels having a first surface, wherein the plurality of support panels are secured directly atop the first set of the plurality of compartments of the base;
a plurality of positioning rails having a plurality of openings along a central axis secured to the first surface of the plurality of support panels;
a plurality of bearings positioned within the openings of the plurality of rails and between the first surface of the support panels, thus the plurality of bearings are retained in the openings and are able to freely rotate in position;
a first spring assembly positioned distal to the first end of the base, comprising:
a first plurality of springs are in a state of tension having a first end a second end,
a spring plate connected to the first end of the first plurality of springs,
a spring plate connected to the second end of the first plurality of springs,
a second spring assembly positioned distal to the second of the base comprising:
a second plurality of springs are in a state of compression having a first end a second end,
a spring plate connected to the first end of the second plurality of springs,
a spring plate connected to the second end of the second plurality of springs,
a plurality of plates disposed directly over each of the support panels and each of the plurality of plates is mechanically connected to one of the sensors, and a first set of the plates connected to the first spring assembly, and a second set of the plates connected to the second spring assembly.

13. The responsive exercise device of claim 12, wherein the plurality of positioning rails are secured to the first surface of the plurality of support panels in a linear fashion across each of the support panels and substantially the same number of positioning rails are secured to each support panel.

14. The responsive exercise device of claim 12, further comprising a first light source attached to the first end of the base.

15. The responsive exercise device of claim 14, wherein when at least one of the plurality of plates displaces from its original position a predetermined distance or rotate a predetermined degree from the original position, the first light source is activated.

16. The responsive exercise device of claim 15, further comprising a second light source attached to the first end of the base.

17. The responsive exercise device of claim 16, wherein when at least one of the plurality of plates move a predetermined distance or rotate a predetermined degree, the second light source is activated.

18. A responsive exercise device comprising:
a base having a first quadrant, a second quadrant, a third quadrant, a fourth quadrant, a first edge, a second edge;
a plurality of sensors, wherein one of the plurality of sensors are placed within each of the quadrants;
a plurality of support panels having a first surface, wherein one of the plurality of support panels are secured in each quadrant and are substantially aligned;
a plurality of positioning rails having a plurality of openings along a central axis secured to the first surface of the plurality of support panels arranged in parallel;
a plurality of bearings positioned within the openings of the plurality of rails and the bearings are able to freely rotate in position;
a first spring assembly positioned between the first quadrant and the second quadrant distal to the first end of the base, comprising:
a first plurality of springs are in a state of tension having a first end a second end,
a spring plate connected to the first end of the first plurality of springs,
a spring plate connected to the second end of the first plurality of springs,
a second spring assembly positioned between the third quadrant and the fourth quadrant and distal to the second of the base comprising:
a second plurality of springs are in a state of compression having a first end a second end,
a spring plate connected to the first end of the second plurality of springs,
a spring plate connected to the second end of the second plurality of springs, and
a plurality of plates, wherein one of the plurality of plates is disposed directly over each of the support panels and mechanically connected to the sensor positioned within that quadrant, and the plates positioned over the first quadrant and the second quadrant are mechanically connected to the first spring assembly and the plates positioned over the third quadrant and the fourth quadrant are mechanically connected to the second spring assembly.

19. The responsive exercise device of claim 18, further comprising a light assembly electrically connected to the sensors, wherein the light assembly is activated upon the movement of the respective plate from a first position to a second position.

20. The responsive exercise device of claim 18, further comprising a speaker electronically connected to the processor, wherein the speaker would produce an audile sound upon the repositioning of at least one of the plurality of plates.

* * * * *